United States Patent
Zhao

(10) Patent No.: US 8,420,113 B2
(45) Date of Patent: Apr. 16, 2013

(54) BIODEGRADABLE MEDICAL DEVICES WITH ENHANCED MECHANICAL STRENGTH AND PHARMACOLOGICAL FUNCTIONS

(75) Inventor: Jonathon Z. Zhao, Belle Mead, NJ (US)

(73) Assignee: Cordis Corporation

( * ) Notice: Subject to any disclaimer, the term of this patent is extended or adjusted under 35 U.S.C. 154(b) by 693 days.

(21) Appl. No.: 11/350,622

(22) Filed: Feb. 9, 2006

(65) Prior Publication Data
US 2006/0264531 A1 Nov. 23, 2006

Related U.S. Application Data

(60) Provisional application No. 60/651,923, filed on Feb. 10, 2005.

(51) Int. Cl.
*A61F 2/92* (2006.01)
*A61F 2/82* (2006.01)
*C08K 3/32* (2006.01)
*C08K 3/40* (2006.01)

(52) U.S. Cl.
USPC .......... 424/426; 523/113; 523/117; 524/415; 524/493

(58) Field of Classification Search .......... 523/113, 523/117; 524/415, 493; 424/426
See application file for complete search history.

(56) References Cited

U.S. PATENT DOCUMENTS

| | | | |
|---|---|---|---|
| 4,820,298 A * | 4/1989 | Leveen et al. | 623/1.18 |
| 5,500,013 A * | 3/1996 | Buscemi et al. | 623/1.22 |
| 5,977,204 A | 11/1999 | Boyan et al. | |
| 6,086,374 A | 7/2000 | Litkowski et al. | |
| 6,165,486 A * | 12/2000 | Marra et al. | 424/423 |
| 6,197,342 B1 | 3/2001 | Thut et al. | |
| 6,203,574 B1 | 3/2001 | Kawamura | |
| 6,244,871 B1 | 6/2001 | Litkowski et al. | |
| 6,319,715 B1 * | 11/2001 | Luo et al. | 435/455 |
| 6,344,496 B1 * | 2/2002 | Niederauer et al. | 523/113 |
| 6,406,498 B1 * | 6/2002 | Tormala et al. | 623/23.75 |
| 6,623,521 B2 * | 9/2003 | Steinke et al. | 623/1.16 |
| 7,479,157 B2 * | 1/2009 | Weber et al. | 623/1.15 |
| 2002/0115742 A1 | 8/2002 | Trieu et al. | |
| 2004/0137075 A1 * | 7/2004 | Fechner et al. | 424/601 |
| 2004/0191292 A1 * | 9/2004 | Chou | 424/426 |
| 2004/0258732 A1 * | 12/2004 | Shikinami | 424/426 |
| 2006/0165754 A1 * | 7/2006 | Ranade | 424/423 |
| 2006/0167540 A1 * | 7/2006 | Masters et al. | 623/1.44 |
| 2007/0061004 A1 * | 3/2007 | Steinke et al. | 623/1.16 |
| 2007/0093895 A1 * | 4/2007 | Donnelly et al. | 623/13.14 |
| 2008/0051866 A1 * | 2/2008 | Chen et al. | 623/1.11 |

FOREIGN PATENT DOCUMENTS

| | | |
|---|---|---|
| WO | WO 98/46164 A1 | 10/1998 |
| WO | WO 00/59559 A1 | 10/2000 |
| WO | WO 01/32072 A2 | 5/2001 |

OTHER PUBLICATIONS

Bellantone et al. "Broad-Spectrum Bactericidal Activity of Ag2O-Doped Bioactive Glass", Antimicrobial Agents and Chemotherapy, vol. 46, No. 6, p. 1940-1945, Jun. 2002.*
European Search Report dated Sep. 25, 2008 for corresponding European Patent Application No. EP 06250728.
Greish, Y.E. et al., "Characterization of Bioactive Glass-Reinforced HAP-Polymer Composites", *J Biomed Mater Res*, 2000, pp. 687-694, vol. 52, John Wiley & Sons, Inc.
Hench, L. et al., "Biocompatibility of Orthopedic Implants", 1982, pp. 67-85, vol. 2, *CRC Press*, Boca Raton, FL.
Wilson, J. et al., "Toxicology and Biocompatibility of Bioglasses", *Journal of Biomedical Materials Research*, 1981, pp. 805-817, vol. 15, John Wiley & Sons, Inc.

* cited by examiner

Primary Examiner — Tae H Yoon

(57) ABSTRACT

The present invention is directed to a medical device, specifically a prosthesis which utilizes a novel class of blends between biodegradable polymers and bioceramics for medical device applications allowing one to capitalize on the biodegradable nature of these two distinct materials while enhancing the strength of these devices through the addition of various amounts of bioactive ceramic and glasses to biodegradable polymers. The blend may be fabricated into a medical device such as a stent or a distal protection device, and may incorporate various agents to enhance radioapacity and/or pharmacological function. In addition, the blend may be used as a coating to a medical device.

3 Claims, 3 Drawing Sheets

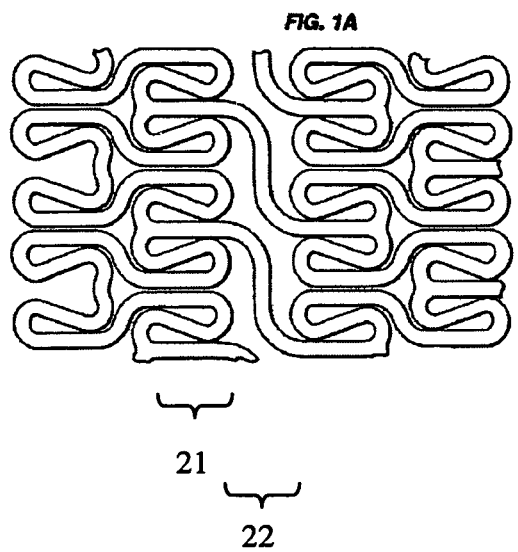
21  22
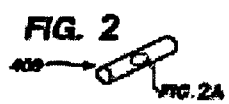
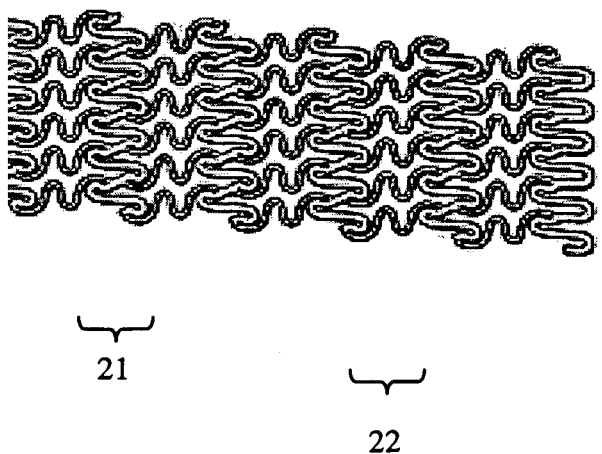
21  22

Substrate

BIODEGRADABLE MEDICAL DEVICES WITH ENHANCED MECHANICAL STRENGTH AND PHARMACOLOGICAL FUNCTIONS

This application claims the benefit of U.S. Provisional Application Ser. No. 60/651,923 filed on Feb. 10, 2005.

BACKGROUND OF THE INVENTION

1. Field of the Invention

The present invention relates to biodegradable devices and methods for fabricating said devices. More particularly, the present invention relates to a biodegradable medical device with enhanced mechanical properties and/or pharmacological functions.

2. Discussion of the Related Art

There exists a large body of literature for the extensive uses of biodegradable and biocompatible polymers for pharmaceutical and medical device applications. Biodegradable polymers are finding increasing uses in medical devices. The safety for use in humans of these biomaterials is evident in the forms of bioabsorbable sutures, controlled release dosage forms such as Lupron depot, etc. Biodegradable materials such as Poly L-Lactic Acid ("PLLA"), Poly D,L-Lactides ("PDLA"), Poly Lactic Glycolic Acid ("PLGA"), Polycaprolactone ("PCL"), Poly Lactide-co-caprolactone ("PLA/CL"), or Poly Lactide/glycolide-co-dioxanone ("PLGA/DO") are known to degrade under physiological conditions Current generation bioabsorbable polymers such as Poly Lactic Acid ("PLA"), Poly(glycolic)acid ("PGA"), which are aliphatic polyesters of poly($\alpha$-hydroxy acids), and Poly Lactic Glycolic Acid/Poly(Lactide-co-glycolide) ("PLGA"), as well as copolymers of PLA, PGA, or PLGA with caprolactone or dioxanone have been used as materials in medical devices with the goal of making the device resorbable and/or absorbable. Specifically these polymers and the related copolymers are the most common bioabsorbable polymers and have been used for the matrices and/or drug carriers for drug eluting stents.

Some examples of such use cited in both patents and publications include U.S. Pat. No. 5,977,204 (incorporated by reference) wherein a biodegradable implant material that comprises a bioactive ceramic is disclosed. The '204 patent discloses blends of surface-passivated bioceramic and biodegradable polymers which include mainly large particles of large porosity for dental and orthopedic applications. U.S. Pat. No. 6,244,871 (incorporated by reference) is another item of some interest in that it discusses Bioactive Glass compositions and methods of treatment using bioactive glass as well as a combination of bioglass and drug delivery vehicles for dental applications. U.S. Pat. No. 6,197,342 (incorporated by reference) discloses the use of biologically active glass as a drug delivery system as well as disclosing a method for impregnating bioglass with drugs for bone applications. U.S. Pat. No. 6,086,374 (incorporated by reference) discloses a Method of treatment using Bioactive glass wherein the treatment of tooth decay is sought to be addressed by using a combination of bioglass and drugs.

In publications such as Wilson, J, et. al., entitled Toxicology and biocompatibility of bioactive glass, JBMR, 1981, 15: 805, and/or Hench, L, et. al., entitled Biocompatibility of orthopedic implants, vol. 2, Boca Raton, Fla. CRC Press, 1982, P 67-85, and/or Greish, Y. and Brown, P. entitled Characterization of bioactive glass-reinforced HAP-polymer composites, Three dimensional, bioactive, biodegradable, polymer-bioactive glass composite scaffolds with improved mechanical properties that support collagen synthesis and mineralization of human osteoblast-like cells in vitro are discussed.

More recently Poly Lactic Glycolic Acid ("PLGA") and other materials have been proposed as materials for stent and drug eluting stent applications. In parallel, bioactive glass and bioceramics are also used for medical device applications in areas of bone replacement and dental care. It is also known that Bioceramics such as BioGlass are commonly used in dental and bone replacement applications and have excellent biocompatibility and safety history with the Food & Drug Administration ("FDA") and that regulatory filings on such products with the FDA exist. While Bioactive glasses have advantages such as bonding rapidly with bone and soft tissues, the disadvantages of bioactive glasses are their brittleness, which limits their uses in weight bearing applications.

Typically these polymeric materials have a very high degree of elasticity and tend to recoil after crimping or expansion. Having a low recoil property is one of many important factors in stent design, thus the high recoil of polymeric materials may not be advantageous. Normally PLLA and PLGA copolymers with a high percentage of LA (Lactic Acid) content as compared to GA (Glycolic Acid), for example a 95%:5% ratio of LA to GA respectively, which results in the copolymer being very brittle and may not easily allow processing into the desired shapes for medical device applications. Although PLGA is more elastic, the mechanical properties such as tensile strength, storage and Young's moduli are decreased with increasing amount of GA or CL (caprolactone). The mechanical properties of Biodegradable polymeric materials may also be negatively impacted by the presence of moisture; in particular, moisture may tend to reduce the modulus of the material. Furthermore, both PGA and PLA copolymers all release acidic products upon degradation resulting in localized acidic conditions in the area of the degrading implant.

Further, there is a need to address and improve filtering devices such as Distal protection devices or Vena Cava filters, both of which whose primary function is to capture and prevent embolic debris from closing off a vessel and ultimately causing tissue death and potentially a heart attack or stroke. With filtration devices such as distal protection and vena cava filters, as the mesh and or pore size of the filtering aspect decreases, more embolic material may become trapped in the filtering mechanism, thereby increasing the load on the filtering portion. While small emboli (typically smaller than 100 microns) are not a major concern because of the body's natural ability to enzymatically degrade, digest or lyse the emboli, the embolic load on the filter itself can be overloaded and result in formation of a thrombus if the blood flow is significantly slowed to the point which allows for a thrombus formation. This thrombus formation if allowed to go unchecked would eventually close off flow to all downstream tissue, which relies upon the vessel in question.

Some other common difficulties with biodegradable stents that may exist are the ability to control the degradation rate of these materials.

SUMMARY OF THE INVENTION

In accordance with the present invention, a means is provided for overcoming the problems associated with the prior art as briefly described above. While the temporary nature of biodegradable materials can enable one to address an ever-widening scope of conditions and allow for the design of temporary devices, these devices should preferably still satisfy various loading conditions, some of which may be significant for polymeric devices. Biodegradable stents may offer several potential advantages over permanent metallic implants. Because biodegradable implants degrade within months of implantation, the issue of long-term metal wear may be eliminated. In addition the risk of late stent thrombosis and the need for long-term anti-platelet therapy may be eliminated.

The present invention utilizes a novel class of blends between biodegradable polymers and bioceramics for medical device applications allowing one to capitalize on the biodegradable nature of these materials while enhancing the strength of these devices thorough the addition of various amounts of bioactive ceramic and glasses. Furthermore, in accordance with one exemplary embodiment of the present invention, blends and combination of blends of these two classes of biocompatible materials may be utilized.

One object of the present invention is directed to address the issue of recoil, more particularly the present invention adds a percentage of biocompatible and bioresorbable materials to make the resulting composite behave more like conventional device materials such as stainless steel (eg: 316L) or cobalt-chromium alloys (eg: L605) thus allowing the medical device to possess properties similar to metals.

Another object of the present invention is related to address the localized acidic condition due to degradation products of biodegradable polymers. Given that PGA and PLA copolymers may release acidic products upon degradation, in accordance with an exemplary embodiment of the present invention the composition and processing conditions may be specified so that the bioactive ceramic or glasses such as bioglass in time will start to leach alkaline ions, thus counteracting the acidic environment resulting in a substantially neutral environment which is beneficial to the surrounding tissue.

In accordance with the present invention, yet another object is the elimination of the need for surface passivation by utilizing sufficiently small particles of ceramic twenty microns (20 um) or less. Moreover, utilization of specific blends and/or combination of blends may be optimized to fine tune degradation rates.

In yet another embodiment of the present invention additives in the form of particles may be added to enhance radiopacity and/or provide a pharmacological benefit. In accordance with an exemplary embodiment of the present invention the proposed biodegradable polymers and bioglass and/or bioceramics blends may be processed into different shapes such as stents or filtering devices and be further enhanced with additional additives providing pharmacological functions such as a drug.

More particularly, benefits and modifications of the present invention include that additional processing steps such as a surface coating with other materials may influence the hydrolysis and degradation rate of the blends.

Furthermore, the present invention when processed into a stent may be modified to provide a stent for bifurcated access. Moreover, in addition to processing the blend into various shapes, the blend itself can be processed as a surface coating encapsulating a medical device.

BRIEF DESCRIPTION OF THE DRAWINGS

FIGS. 1a through 4a show some examples of stent configurations. In each of these figures, the stent is indicated by item 400.

DETAILED DESCRIPTION OF THE PREFERRED EMBODIMENTS

Figure 3A:
Figure 4:
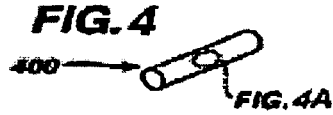
Figure 4A:
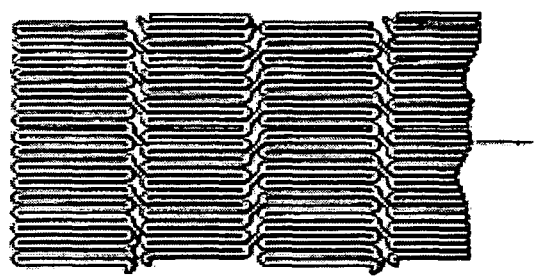

As used herein, biodegradable is meant to mean biodegradable, bioerodible, and/or bioresorbable. In this fashion, a biodegradable material may degrade, resorb, or erode through either a bulk mechanism of action, surface mechanism of action, or combination of the two.

In accordance with an exemplary embodiment of the present invention the proposed biodegradable polymers and bioglass and/or bioceramics blends require a fine suspension of bioglass or bioactive ceramic particles in polymer solutions for processing, or alternately a fine mixture of the two for extrusion and injection molding processes. The mechanical properties of the blends are a function of the ratio between the two materials. Thus the mechanical properties may be tuned as a result of varying the ratio between the materials. Having a greater percentage of biodegradable polymers relative to bioactive ceramic particles may allow for improved mechanical properties while maintaining acceptable biodegradation rates. Increasing the percentage of bioactive ceramics to approximately 20%+/−5% of the total volume of material may improve the mechanical properties of the material formed from such a blend, while the slightly basic nature of the degrading bioglass may also serve to act as an inherent stabilizer of the degrading polyester.

Many bioactive ceramics are defined in the literature. Examples include the BioGlass series from US-Biomaterials, those having small particle sizes are preferred. Other important items to note include: the biodegradable ceramics and/or bioglass which preferably have sufficient small diameters to ensure proper mixing for device applications, in the range of less than 20 microns and into the nanometers range. Processing methods to create nano-sized particles may be applicable; the weight ratio between the biodegradable polymers and bioceramics and bioglass may range be between 99%-1% to 1%-99%; biologically active compounds such as drugs, proteins, genes may be incorporated into the matrices of the proposed blends, or applied to the surface of, or partially cover the surface of, a device made from the blends; the blends have sufficiently even mixing that they exhibit preferred properties such as enhanced tensile strength, storage and Young's moduli, and sufficient thermal stability.

Additionally, the degradation products of each of the blending materials may serve to neutralize each and/or the combination to create milder environment and consequently improved biocompatibility. This may be accomplished by adjustment and specification of the composition and processing conditions so that the bioactive ceramic or glasses such as bioglass in time will start to leach Calcium (Ca) & Sodium (Na) ions thus making the surrounding environment more alkaline. This has the additional benefit of resulting in an increasing pH at least in the local area of the device, which may serve to neutralize the typical acidic conditions that potentially result due to the degradation of the PGA, PLA, PLGA or similar biodegradable matrices. The non-passivated surface of the bioactive ceramic may serve as a neutralizing agent for progressively acidic environment caused by the degrading polymer components, resulting in a more controlled degradation rate and improved biocompatibility. Thus the overall pH of the immediate local area around the degradation products may be made substantially neutral which is beneficial to the surrounding tissue as compared to solely acidic or basic environments.

Figure 5A:
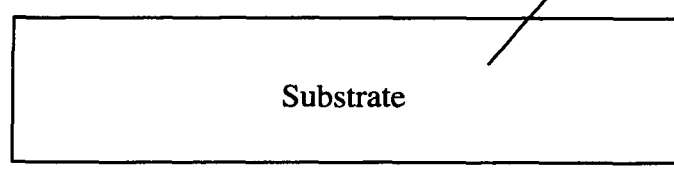
FIGS. 5a and 5b represents a cross sectional schematic of a portion of a medical device both without and with a surface coating.
Figure 5B:
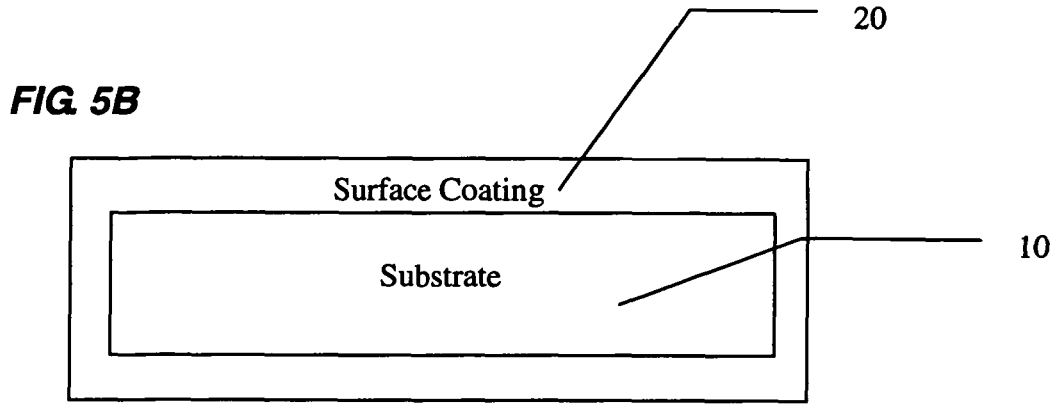

Once the blends are produced, regular processes such melt press, extrusion, film casting may be used to process the blends into different forms and shapes such as slotted tubes, rods, films, sheets, etc. The resulting material may be processed into different shapes such as tubes for further processing. One example of further processing is laser cutting that may be used to process the material into different forms. Ultimately, medical devices may be fabricated from the material. Alternatively the resulting blend may be processed as a surface coating and used to encapsulate both non-degradable and degradable medical devices. In FIGS. 5a and 5b a representation of a cross-section of a medical device member is shown. Specifically, FIG. 5a shows the rectangular cross-section representation of a band (21) or link (22) of a stent (400), we see that the resulting biodegradable blend may be used to form all or portions of the substrate (10). Alternately, as shown in FIG. 5b, the resulting biodegradable blend may be used to form the surface coating (20) which may then encapsulate the substrate (10) which may also be formed from a biodegradable blend in accordance with the present invention or alternately the substrate may be formed from more traditional materials such as non-degradable polymers, or metals such as nitinol, stainless steel, or colbalt-chromium alloys Medical devices such as stents (400) and/or filtering devices fabricated from such a material are not only biocompatible and bioresbrbable, they also exhibit excellent and/or enhanced mechanical properties relative to biodegradable polymeric devices without the addition of bioceramic particles.

Specifically as it relates to stents (400), the present invention adds a percentage of biocompatible and bioresorbable materials to make the resulting composite behave more like conventional device materials and thus mitigate the extent of recoil. Thus the blends of these biodegradable and bioresorbable materials would allow a resorbable drug eluting stent to be more easily crimped and expanded thus reducing the extent of recoil as compared to a polymeric stent alone.

In accordance with an exemplary embodiment of the present invention, the addition of bioceramics and/or bioglass may enhance the mechanical strength and make the blends behave more like metals, which have characteristics that are desirable for crimping and expansion behaviors and thus also serve to increase the mechanical properties of the material. Unique features of the present invention include: biodegradable polymers and/or copolymers blended with non-surface passivated bioactive ceramic blend for improved mechanical properties as medical device materials. The resulting blends should have increased ductility and be more amenable to crimping and balloon expansion. Composites of bioactive glass, may reinforce hydroxyapatite and polymers have been shown to possess improved mechanical properties. Both tensile strength and the elastic modulus may be increased with the addition of up to 10% bioactive glass.

A stent (400) is commonly used as a tubular structure left inside the lumen of a duct to relieve an obstruction. Commonly, stents (400) are inserted into the lumen in a non-expanded form and are then expanded autonomously (or with the aid of a second device) in situ. A typical method of expansion occurs through the use of a catheter mounted angioplasty balloon, which is inflated within the stenosed vessel or body passageway, in order to shear and disrupt the obstructions associated with the wall components of the vessel and to obtain an enlarged lumen. Stents may also be fabricated from super-elastic and/or shape memory alloys such as nitinol, such stents are known as self-expanding stents.

In the absence of a stent, restenosis may occur as a result of elastic recoil of the stenotic lesion. Although a number of stent designs have been reported, these designs have suffered from a number of limitations. Some of these limitations may be addressed by the use of biodegradable stents in accordance with the present invention. Such stents may be expanded during or just after balloon angioplasty. As a general rule, the manufacture of a stent will need to compromise axial flexibility in order to permit expansion and provide overall structural integrity.

Stents typically have a first end and a second end with an intermediate section between the two ends. The stent further has a longitudinal axis and comprises a plurality of longitudinally disposed bands (21), wherein each band defines a generally continuous wave along a line segment parallel to the longitudinal axis. A plurality of links (22) maintains the bands in a tubular structure. In a further embodiment of the invention, each longitudinally disposed band (21) of the stent is connected, at a plurality of periodic locations, by a short circumferential link (22) to an adjacent band. The wave associated with each of the bands (21) has approximately the same fundamental spatial frequency in the intermediate section, and the bands (21) are so disposed that the waves associated with them are spatially aligned so as to be generally in phase with one another. The spatial aligned bands (21) are connected, at a plurality of periodic locations, by a short circumferential link (22) to an adjacent band. In particular, at each one of a first group of common axial positions, there is a circumferential link (22) between each of a first set of adjacent pairs of bands (21). At each one of a second group of common axial positions, there is a circumferential link (22) between each of a second set of adjacent rows of bands (21), wherein, along the longitudinal axis, a common axial position occurs alternately in the first group and in the second group, and the first and second sets are selected so that a given band is linked to a neighboring band at only one of the first and second groups of common axial positions.

Furthermore, this stent (400) may be modified to provide for bifurcated access, whereas the stent (400) itself is uniform throughout. If the manufacturer designs such a stent to have a large enough opening, then it is possible to place the stent such that a pair of stents may be placed one through the other. In this fashion, the stents are capable of being placed at a bifurcation, without any welding or any special attachments. An interlocking mechanism may be incorporated into the stent design to cause the stent to interlock at the desired position during assembly of the device. Further, a metallic stent has been designed which contains a repeating closed loop feature. The stent is designed such that the closed loop does not change dimensions during expansion. The composite stent is created by filling the area enclosed by the loops with a material that enhances clinical performance of the stent. The material may be a ceramic or a polymer, and may be permanent or absorbable, porous or nonporous and may contain one or more of the following: a therapeutic agent, a radio-opaque dye, a radioactive material, or a material capable of releasing a therapeutic agent, such as rapamycin, cladribine, heparin, nitrous oxide or any other known drugs, either alone or in combination. It has been seen, however, that it may be desirable to provide for stents that have both flexibility to navigate a tortuous lesion as well as increased column strength to maintain the rigidity necessary after placement into the vessel lumen of the body. The preferred designs tend to provide the flexibility via undulating longitudinal connectors (22). The rigidity is generally provided via the mechanism of slotted tubular stents. It is perceived that there may be mechanisms capable of enhancing the characteristics of these types of stents. Such a stent would be both flexible in delivery and rigid upon placement/implantation.

Furthermore, it is desirable to be able to produce stents (400) and/or filtering devices in which the cross-sectional profile of either the struts (21) or the connecting members (22) is tapered (or variable) in size. In addition, it may be desirable to modify stents and/or filtering devices to have non-rectangular cross-sections. In both these cases, different manufacturing methods may aid in the creation of such stents and the use of polymeric material may provide additional processing flexibility.

Specific benefits of the present invention include medical devices made from the proposed blends that may be amenable to additional processing such as crimping and expansion. The extent of mechanical property changes may partly depend on the particle size and blending ratio of the bioceramic particles. The degradation rate of the blends may be modulated by a number of variables which include but are not limited to the composition of the polymeric materials, the molecular weight of the polymers, the blending ratio between the polymer and the bioceramics and bioglass, the inclusion of additional functional entities such as a drug or a contrasting agent, as well as any combination of the above items either individually or as a group.

In accordance with the present invention, it may be highly desirable to provide additives such as radiopaque agents in the form of particles. Barium-sulfate particles are one such compound that may enhance radiopacity, and also have the added benefit of acting as a hydrophobic barrier which alone or in combination with particles sized sufficiently small also allows for maintaining the modulus of the bioceramic material without surface passivation. These additional additives/compounds such as contrasting agents may be incorporated into the blends to serve additional functions such as modulation of hydrolysis of the matrices and radiopacity.

Surface passivation of the bio-ceramic particles is not required and additional processing steps may be used to further modify the structural, hydrolytical, and pharmaceutical behaviors of the blends. Utilization of sufficiently small particles of bioactive ceramic (20 um or smaller) results in eliminating the need for surface passivation of the bioceramic particles because the small size allows a blend to be created with biodegradable polymeric particles or alternately allowing for a biodegradable polymeric solution to be created which is less affected by the presence of moisture. By minimizing and/or eliminating the impact of the presence of moisture, one may also minimize the impact on the modulus of the material since moisture may tend to reduce the modulus of the bioceramic material.

The incorporation or application of biologically active or pharmaceutically active compounds with the present invention is a further object of this invention and is an improvement to methods and/or devices which require the use of a conduit to deliver the agent to the desired location. Additional pharmacologically active compounds such as small molecular weight compounds, proteins, gene plasmids etc. may be incorporated into the matrices of the blends, or added in at a later stage. The porosity of the blended bulk material, and the surface morphology of the blend matrices may be modified so that drugs may be optimally incorporated, alternately the surface may be modulated to achieve optimal biocompatibility. A chosen drug with specific functions in treating cardiologic and peripheral vascular diseases may be added through spray coating or dip-coating onto the medical devices. Different levels of drugs may be incorporated into the matrices of the blends, or added at a later stage to modulate the release kinetics, while different release kinetics may be achieved by drug loading level and combination of drugs, use of a diffusion regulation layers etc. It is important to note that the use of bioceramics will likely change the drug release rate as well. Alternately these drugs may also be incorporated into the devices during the blending process eliminating the need for additional and costly process steps.

Compounds such as those identified below may be applied as coatings on these devices or incorporated within the material during the blending process and may be used to deliver therapeutic and pharmaceutical agents which may include: anti-proliferative/antimitotic agents including natural products such as vinca alkaloids (i.e. vinblastine, vincristine, and vinorelbine), paclitaxel, epipidophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The processed medical devices may be further impregnated with biologically active species such as drugs, proteins, and/or genes for enhanced pharmacological actions during the blending process or any subsequent steps.

The density and porosity of the blends may be adjusted to modulate the degradation time and resorption rate in vivo. Bioceramic of different particles sizes, especially the small diameters may be used to make the blends and thus impart different mechanical properties of the final resulting composite. Bioceramics of different compositions may also be used for blending in order to obtain composites of different properties such as modulated interfacial morphology with the biodegradable domains, and subsequent modulation of the degradation time of the composites. Different ratios of the bioceramic and biodegradable polymers may be used for blending to achieve different mechanical strengths and degradation time. Different processing conditions may be used to make the blends with different physical and surface properties such as porosity, density and contoured surface properties. The biological activity of the bioglass may be modulated by passifying the surfaces of the bioglass particles. This will result in the degradation time and neutralizing effects of such bioglass particles being changed as well. Various polymers may be used to adjust the degradation time without excessive concerns of the mechanical properties since the mechanical properties may be enhanced by the use of the bioceramic. A shortened degradation time without a decrease of mechanical strength is crucial to the overall performance of the blends as medical devices such as drug eluting stents. Lastly the addition of dioxanone may alter or modulate the degradation rate or in this case the hydrolysis rate of the biodegradable polymers. Moreover, additional pharmacological functions may be easily incorporated into the blend.

The use of compounds in conjunction with the present invention can provide distinct clinical advantages over existing therapies and/or devices. More specifically, compounds that are capable of causing lysis or degradation of the embolic debris may be incorporated into the material when the material is formed into a medical device used for filtering such as a vena cava filter or a distal protection device. A factor to consider in the selection of such a compound is the origin of the debris be it thrombus, plaque, atheroma, or any other form representing an embolus. As the mesh and or pore size of the filtering aspect decreases, more embolic material may become trapped in the filtering mechanism, thereby increasing the load on the filtering portion. While small emboli (typically smaller than 100 microns) are not a major concern because of the body's natural ability to enzymatically degrade, digest or lyse the emboli, the embolic load on the filter itself can be overloaded and result in formation of a thrombus if the blood flow is significantly slowed to the point which allows for a thrombus formation. In this situation the incorporation or application of compounds, which can degrade trapped emboli, can be beneficial. Some exemplary suitable compounds may include: Tissue Plasminogen(TPA); Streptokinase(SK); Reteplase; Tenecteplase; Urokinase; Lanoteplase; Staphylokinase; and/or Nadroparin(anti-factor Xa). In addition, the filtering portion may incorporate an antithrombotic and/or antithrombogenic agent to prevent the formation of a thrombus. Some exemplary compounds may include: Heparin; Fragmin (dalteparin, low MW Heparin); a monoclonal antibody such as ReoPro™ (abciximab, anti-platelet antibodies) Acenocoumarol; Anisindione; Dicumarol; Warfarin; Enoxaparin (Lovenox); Anagrelide (Agrylin); Indomethacin (Indocin); Dipyridamole; Clopidogrel; Aggrenox; and/or Coumadin. Furthermore, an affinity-binding compound may also be incorporated with the filtering aspect by itself or in combination with other compounds. Affinity-binding compounds can promote the binding and/or adhesion of embolic material thus facilitating entrapment of embolic material and subsequent removal from the blood stream. Whether incorporated into the material by methods such as chemical surface treatments, bombardment, placement into reservoirs, or in the case of polymeric devices blended with the material itself, or by application of a coating to the devices with a compound, any identified compound or combination of identified compounds may be used. Furthermore any number of compounds may suggest themselves to one who is skilled in the art and may be utilized in connection with the present invention alone or in combination with other compounds.

In accordance with an exemplary embodiment of the present invention the proposed biodegradable polymers and bioglass and/or bioceramics blends may be processed into different shapes such as stents and/or filtering devices and be further modified with a degradation and/or diffusion barrier or barriers. A preferred mode of further modification is utilization of a coating of the device with additional degradable polymers to modulate the degradation rates of the blends.

Alternatively, other known biodegradeable polymers include but are not limited to polyphosphoesters, polyanhydrides, polyorthoeseters, polycarbonates, or the polymer blends of them, as well as other naturally derived polymers such as proteins, or polypeptides which may be utilized in accordance with an exemplary embodiment of the present invention.

In another alternative embodiment, blends of these two classes of biocompatible materials may be utilized, and testing may be utilized to verify that the blends of these two biocompatible and biodegradable materials are also biodegradable and biocompatible.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A medical device comprising an intravascular stent configured as a substantially tubular structure defining a longitudinal axis and having a plurality of longitudinally disposed bands, wherein each band defines a generally continuous wave along a line segment parallel to the longitudinal axis, and a plurality of links that maintain the plurality of bands in a tubular structure, wherein the stent is formed from an inorganic/organic blend including bioactive ceramic particles in an amount ranging from 15 to 25 percent of the blend by volume and biodegradable polymer particles in an amount ranging from 75 to 85 percent of the blend by volume, wherein each of the bioactive ceramic particles is equal to or less than 20 microns in size.

2. The medical device according to claim 1, wherein the blend further comprises a radiopaque agent.

3. The medical device according to claim 1, wherein the blend further comprises a pharmaceutical agent.

* * * * *